United States Patent
Corbett

(10) Patent No.: US 10,119,910 B2
(45) Date of Patent: Nov. 6, 2018

(54) PARTICLE CHARACTERISATION INSTRUMENT

(71) Applicant: Malvern Instruments Limited, Worcestershire (GB)

(72) Inventor: Jason Cecil William Corbett, Worcestershire (GB)

(73) Assignee: MALVERN PANALYTICAL LIMITED, Malvern, Worcestershire (*) Notice: Subject to any disclaimer, the term of this patent is extended or adjusted under 35 U.S.C. 154(b) by 91 days.

(21) Appl. No.: 14/879,820

(22) Filed: Oct. 9, 2015

(65) Prior Publication Data

US 2017/0102329 A1    Apr. 13, 2017

(51) Int. Cl.

| | |
|---|---|
| G01N 21/00 | (2006.01) |
| G01N 21/64 | (2006.01) |
| G01J 3/44 | (2006.01) |
| G01N 15/02 | (2006.01) |
| G01N 21/51 | (2006.01) |
| G01N 21/83 | (2006.01) |

(Continued)

(52) U.S. Cl.
CPC .......... *G01N 21/64* (2013.01); *G01J 3/4406* (2013.01); *G01N 15/0211* (2013.01); *G01N 21/51* (2013.01); *G01N 21/645* (2013.01); *G01N 21/83* (2013.01); *G01J 2003/1217* (2013.01); *G01N 2015/0222* (2013.01); *G01N 2021/4792* (2013.01); *G01N 2021/6417* (2013.01); *G01N 2021/6471* (2013.01)

(58) Field of Classification Search
CPC ................. G01N 21/64; G01N 2021/6417
USPC ...................................... 250/459.1
See application file for complete search history.

(56) References Cited

U.S. PATENT DOCUMENTS

| 5,017,497 A | 5/1991 | Gerard de Grooth et al. |
| 5,104,221 A | 4/1992 | Bott et al. |

(Continued)

FOREIGN PATENT DOCUMENTS

EP    1112481    7/2001

OTHER PUBLICATIONS

McCully et al. ("NIRCam Filter Wheels" Cryogenic Optical Systems and Instruments XI, edited by James B. Heaney, Lawrence G. Burriesci, Proc. of SPIE, vol. 5904. Aug. 2005, pp. 59040B-1 to 59040B-5).*

(Continued)

*Primary Examiner* — David Porta
*Assistant Examiner* — Meenakshi Sahu
(74) *Attorney, Agent, or Firm* — Morrison & Foerster LLP

(57) ABSTRACT

An instrument and a method for measuring the characteristics of particles in a sample. The instrument comprises a light source operable to provide a light beam and defining an illumination axis; a sample cell placed on the illumination axis; a scattered light detector positioned to receive scattered light along a detection path from a sample in the sample cell, the scattered light produced by the interaction of the light beam with the sample; and a filter changer positioned between the sample cell and the scattered light detector. The filter changer comprises at least one optical filter and an actuator. The actuator is operable to move each of the at least one optical filter between a first position in which the detection path does not pass through the optical filter, and a second position in which the detection path passes through the optical filter.

18 Claims, 4 Drawing Sheets

(51) Int. Cl.
 G01J 3/12 (2006.01)
 G01N 21/47 (2006.01)

(56) References Cited

U.S. PATENT DOCUMENTS

| | | |
|---|---|---|
| 6,404,493 B1 | 6/2002 | Altendorf |
| 6,515,289 B1 * | 2/2003 | Kask .................. G01N 21/6408 |
| | | 250/459.1 |
| 6,939,515 B2 * | 9/2005 | Carlson ................ B01J 19/0046 |
| | | 210/321.6 |
| 7,956,998 B2 | 6/2011 | Plant |
| 8,717,562 B2 | 5/2014 | Smart et al. |
| 9,052,261 B2 | 6/2015 | Smart et al. |
| 2005/0172887 A1 * | 8/2005 | Betzel ....................... C30B 7/00 |
| | | 117/1 |
| 2008/0285032 A1 * | 11/2008 | Ohkubo ............. G01N 15/0205 |
| | | 356/343 |

OTHER PUBLICATIONS

N.C. Ford, Jr. "Light Scattering Apparatus", Chapter 2 in Dynamic Light Scattering. Ed. R. Pecora, Plenum (1985), 52 pages.

* cited by examiner

PARTICLE CHARACTERISATION INSTRUMENT

FIELD OF THE DISCLOSURE

The disclosure relates to an instrument for characterising particles, particularly to an instrument including an automated optical filter changer for dynamic light scattering or florescence correlation spectroscopy measurements.

BACKGROUND

Dynamic light scattering (DLS) is a powerful technique for measuring the size of particles, for example nanomaterials and nanoparticulates. Typically, a suspension or solution containing the particles is placed in a transparent sample cuvette and is illuminated with a vertically polarised laser beam. Light scattered from the particles along a particular direction is detected in a plane orthogonal to the polarisation of the incoming light, and analysed using well known methods to determine properties of the particles. For example, light that is back-scattered from the particles may be detected, and/or light that is forward scattered and/or side-scattered (e.g. scattered light at an angle of 90° to the incoming light).

A further development of dynamic light scattering, depolarised dynamic light scattering (DDLS), seeks to quantify the anisotropy in scattering from particles that deviate from a sphere of uniform refractive index, such as rods, ellipsoids, discs, or spherical Janus particles. In DDLS, a particular polarisation of scattered light is detected. For example, a sample may be illuminated with vertically polarised light, and the correlation function of the scattered light detected in each scattered polarisation, separately, along the detection path.

There are many laboratory instruments available that can perform dynamic light scattering, such as the Malvern Zetasizer® range. However, these instruments may not be able to measure different polarisation states of the scattered light, and so cannot perform depolarised dynamic light scattering measurements. Upgrading system hardware, or replacing a system altogether in order to perform DDLS may be undesirably expensive.

Further information about the particles in a solution can be found from fluorescence correlation spectroscopy (FCS), which uses a correlation analysis of fluctuations in florescence emitted by the particles to determine particle dynamics. The equipment needed to perform FCS is similar to that for DLS, but requires an appropriate set of optical filters to be used to analyse the scattered light.

SUMMARY OF THE DISCLOSURE

There is provided an instrument for measuring the characteristics of particles in a sample, the instrument comprising: a light source operable to provide a light beam and defining an illumination axis; a sample cell placed on the illumination axis; a scattered light detector positioned to receive scattered light along a detection path from a sample in the sample cell, the scattered light produced by the interaction of the light beam with the sample; and a filter changer positioned between the sample chamber and the scattered light detector. The filter changer comprises: at least one optical filter; and an actuator for moving the at least one optical filter between a first position in which the detection path does not pass through the optical filter, and a second position in which the detection path passes through the optical filter.

In some embodiments, the instrument may for example be for performing depolarised dynamic light scattering measurements. Additionally or alternatively, the instrument may be for performing fluorescence correlation spectroscopy measurements.

The filter changer may be used to place an optical filter into, or remove an optical filter from the path of the scattered light, or to change the filter that is in the path of the scattered light. For example, standard DLS measurements are undesirably sensitive to any fluorescence produced by the illuminated particles in the sample. If the particles produce a large amount fluorescence, the filter changer may be used to move a fluorescence filter, such as a narrow band filter, into the path of the scattered light to limit the intensity of fluorescence that reaches the detector. On the other hand, if the particles do not produce a large amount of fluorescence when illuminated at the wavelength of the light source, it may be undesirable to have a florescence filter in the path of the scattered light, as it may degrade the DLS measurement. The filter changer may then be used to move the florescence filter out of the path of the scattered light.

In some embodiments, the filter changer may comprise a rotatable wheel, the wheel comprising a plurality of filter mounts for holding a plurality of optical filters, and wherein the actuator is operable to rotate the wheel so as to move each filter between the first and second positions. The wheel may comprise a plurality of filter mounts for holding optical filters. For example, the plurality of filter mounts may be arranged circularly around the centre of the wheel so that the filter mount in the illuminated position may be changed by rotating the wheel.

In some embodiments, the at least one optical filter may comprise at least one of: a polarising filter, a fluorescence filter, a band-stop filter, a band-pass filter, a high-pass filter or a low-pass filter. The filter or filters may be removable by a user.

In some embodiments, the at least one optical filter may comprise a first polarising filter and a second polarising filter. For example, an axis of polarisation of the first polarising filter, when in the second position, may be orthogonal to an axis of polarisation of the second polarising filter, when in the second position. For example, one of the polarising filters, when in the illuminated position, may transmit only the vertical component of scattered light. The other polarising filter, when in the illuminated position, may transmit only the horizontal component of scattered light. Such embodiments may allow a DDLS measurement to be performed using an existing DLS instrument.

The scattered light detector may be positioned to receive back-scattered light (e.g. light that is scattered within a range of 160°-200° from the direction of the incoming light beam), side-scattered light (e.g. light that is scattered light within a range of 70°-110° from the direction of the incoming light beam), or forward-scattered light (e.g. light that is scattered light within a range of 0°-20° from the direction of the incoming light beam). The detector may be positioned to receive any other angle of scattered light.

The instrument may be for performing at least one of: a dynamic light scattering measurement, an electrophoretic light scattering measurement, and a static light scattering measurement. The instrument may be for performing depolarised dynamic light scattering measurements. The instrument may be for performing fluorescence correlation spectroscopy measurements.

In some embodiments the actuator may comprise a motor. The instrument may comprise a controller to control the filter changer. The controller may comprise a processor configured to control the operation of the filter changer. The controller may, for example, comprise a processor for automating the control and recording of an experiment, for example the detector may also be connected to the processor.

The controller may be operable to control the filter changer to move the at least one optical filter between the first and second positions during characterisation of a sample. The controller may be operable, during characterisation of a sample, to change which of the at least one filter is in the second position. The controller may be operable, during characterisation of a sample, to switch which of a first polarising filter and a second polarising filter are in the second position.

The instrument may comprise an auto-titrator, for performing a titration during a measurement sequence. The instrument may be configured to characterise the sample as titration of the sample is performed, so as to determine a change in the characteristics of the properties of the particles as a function of the titration.

The instrument may comprise an auto-sampler, configured to position each of a plurality of samples in the illumination axis so as to perform a measurement on a plurality of samples. The instrument may be configured to use the controller to use more than one filter in the course of characterising each sample, or to use different filters to characterise different samples.

According to a second aspect of the disclosure there is provided a method of measuring the characteristics of particles in a sample, the method comprising: placing the sample in a sample cell; illuminating the sample with a light beam from a light source so as to produce scattered light by the interaction of the light beam with the sample; moving an optical filter into a scattered light detection path between the sample and a detector using a filter changer, the filter changer comprising an actuator for moving the optical filter into the detection path; and filtering the scattered light along the detection path with the optical filter; and detecting the scattered light that has passed through the optical filter with the detector.

In some embodiments, the optical filter may be a first optical filter, and the filter changer may comprise a plurality of optical filters. The method may further comprise: moving a second optical filter of the plurality of optical filters into the detection path; and detecting the scattered light that has passed through the second optical filter with a detector.

Moving the second optical filter into the detection path may comprise moving the first optical filter out of the detection path.

The filter changer may comprise a rotatable wheel, and wherein moving a second optical filter into the illuminated position comprises rotating the wheel.

In some embodiments, the optical filter comprises at least one of: a polarising filter, a fluorescence filter, a band-stop filter, a band-pass filter, a high-pass filter or a low-pass filter.

DETAILED DESCRIPTION

Representative examples are described in further detail below, with reference to the accompanying drawings, in which.

Figure 1:
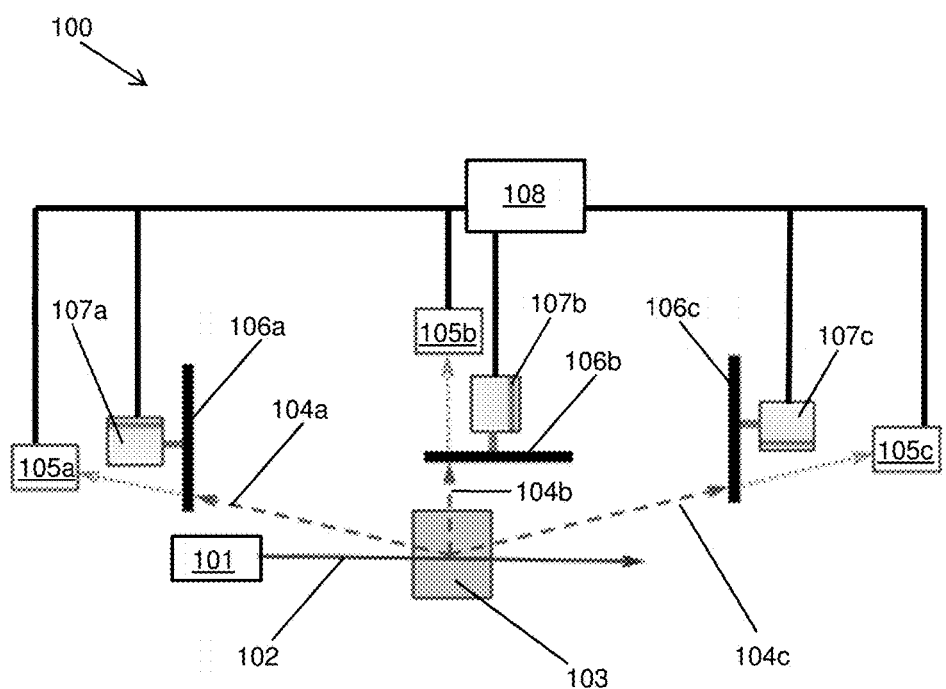
FIG. 1 is a schematic representation of an exemplary embodiment of an instrument comprising a plurality of detectors and filter changers.

FIG. 1 shows an exemplary embodiment of an instrument 100. A light source 101 produces a light beam 102 that illuminates a sample in a sample cell 103. The light source 101 may for example be a laser. The light source 101 may for example produce light with a wavelength in the range 280-2000 nm.

The light beam 102 interacts with the sample in the sample cell 103. This interaction may cause the light to be scattered, for example, or fluorescence to be emitted. The light may be scattered or emitted along any direction relative to the direction of the light beam 102. In the illustrated embodiment, light scattered at along three different detection paths, at three different angles, is detected—backscattered light 104a, side-scattered light 104b, and forward scattered light 104c. These beams of scattered light are detected by detectors 105a, 105b, and 105c respectively. Detectors 105a-c may for example be photodiodes (e.g. avalanche photodiodes), and may output a signal to a processor for recording the intensity of detected light. Although three detectors 105a-c are shown in the illustrated embodiment, any number may be used. For example, only one detector may be used, placed at one of the positions of detectors 105a-c. Alternatively two or more detectors may be used. Detectors may be placed to measure any angle of scattered light. The detectors 105a-c are connected to a processor 108. Processor 108 may record the signal measured by detectors 105a-c.

Between the cell 103 and each detector 105a-c there is a filter changer 106a-c. The filter changers 106a-c may each comprise a filter mount for holding an optical filter, or a plurality of filter mounts each for holding an optical filter. Filter changers 106a-c are each positioned so that the detection path for scattered light beams 104a-c may pass through an optical filter of the respective filter changer 106a-c. Filter changers 106a-c are actuated by actuators 107a-c respectively. Actuators 107a-c may be controlled by a controller, for example a controller included in processor 108. Although three filter changers are shown in FIG. 1, any number of filter changers may be used. In particular, the number of filter changers may match the number of detectors. Alternatively, multiple filter changers may be placed on a single detection path, for example if a plurality of filters is required for a given measurement of the scattered light.

Figure 2A:
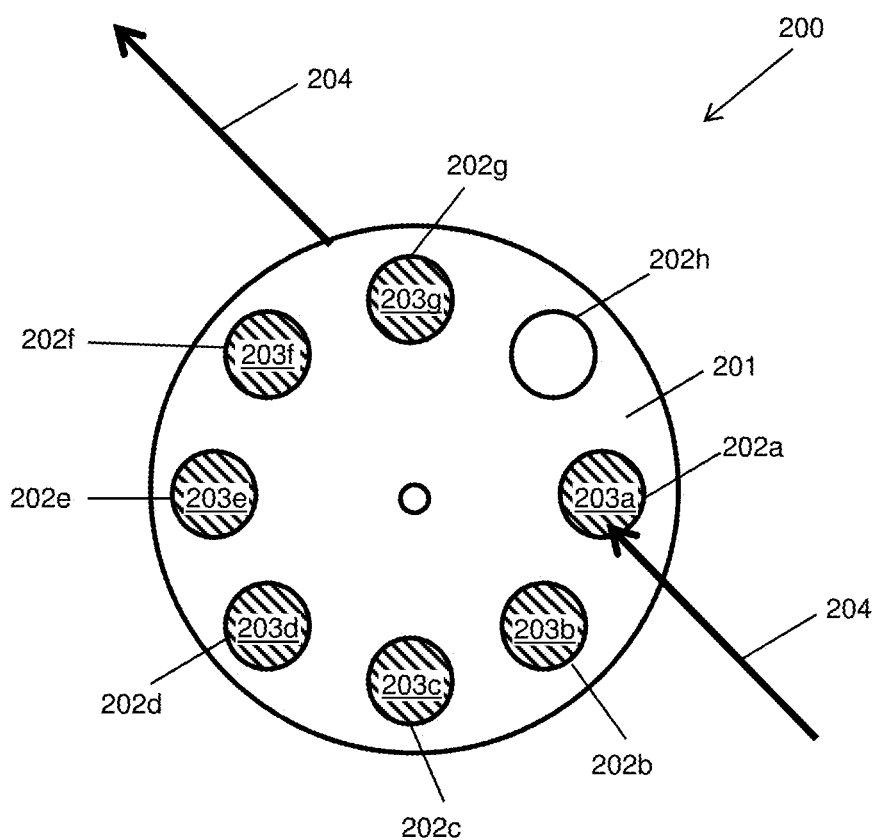
FIG. 2a is a schematic representation of an exemplary filter changer.
Figure 2B:
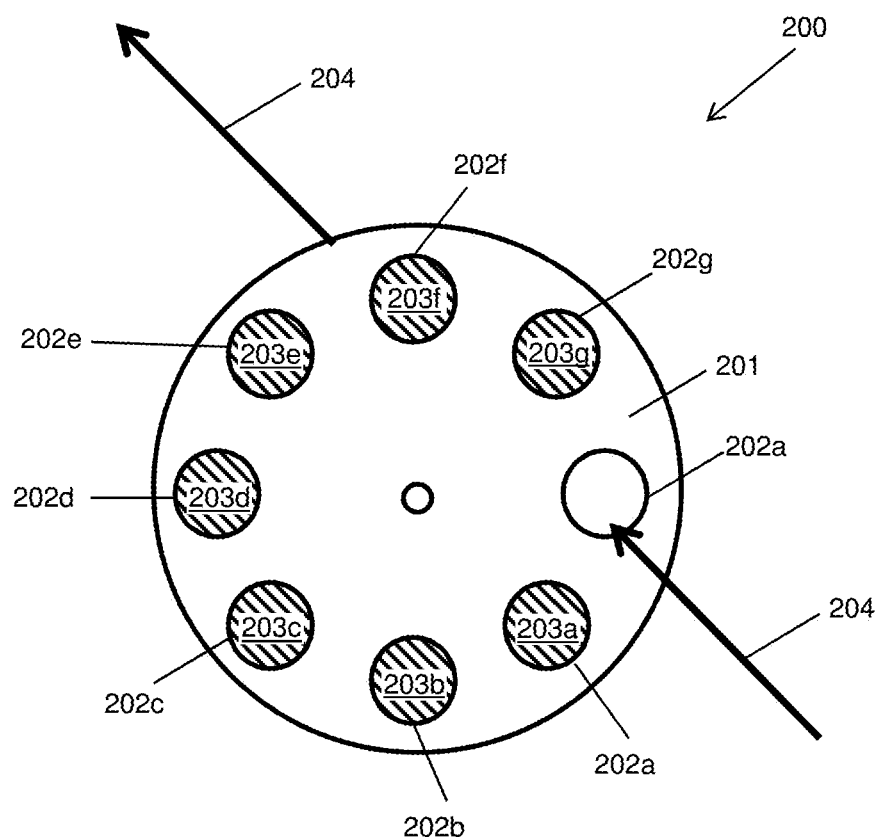
FIG. 2b is a schematic representation of the filter changer of FIG. 2a in an alternative position.

FIGS. 2A and 2B illustrate an exemplary embodiment of a filter changer 200 that may be used in an instrument, for example instrument 100. Filter changer 200 comprises a rotatable wheel 201 and a plurality of filter mounts 202a-h. The filter mounts 202a-h are arranged circularly around the centre of wheel 201. In the illustrated embodiment, filter mounts 202a-h are arranged with rotational symmetry around the centre of wheel 201. The illustrated embodiment comprises eight filter mounts 202a-h, but any number of mounts is possible, for example two, three, four, five, six, seven, nine, or ten filter mounts. Although filter changer 200 comprises a rotatable wheel 201, in other embodiments the filter changer may be differently shaped, and may be configured to move differently to place a filter into a detection path. For example, a filter changer may comprise a plurality of filters arranged in a row, with the actuator of the filter changer adapted to move the filters linearly in a direction that is orthogonal to the detection path.

In the illustrated embodiment, filter mounts 202a-g each contain an optical filter, 203a-g. Any of the optical filters may comprise, for example, a polarising filter, a fluorescence filter, a band-stop filter, a band-pass filter, a high-pass filter or a low-pass filter. The optical filters maybe removable by a user, or may be fixed in the filter changer 200. Filter mount 202h may not contain an optical filter, but may instead be left empty. This may be useful for measurements which do not require an optical filter, to avoid any degradation of detected signal due to the optical filters.

In FIG. 2A, wheel 201 is orientated so that a detection path 204 passes through optical filter 203a. The detection path 204 may, for example, correspond with any of beams 104a-c in instrument 100. The wheel 201 may be rotated around its centre so that a different filter 203b-g, or an empty filter mount 202h, is in the detection path 204, so that scattered light beam 204 passes through the different filter or empty mount. For example wheel 201 may be rotated clockwise or anti-clockwise about the centre of wheel 201. This is shown in FIG. 2B, where wheel 201 has been rotated so that the empty filter mount 202h is in the detection path 204. In this case, scattered light beam 204 does not pass through an optical filter.

The wheel 201 may be rotated by an actuator such as a motor. The actuator may be controlled by software on a processor, for example processor 108, that allows automated measurements to be run. For example, the processor may communicate with a controller that is operable to control the actuator of the filter changer 200. Alternatively the controller may be included in the processor. The processor may determine a desired orientation of the wheel 201, so scattered light beam 204 passes through a particular filter 203a-g or filter mount 204a-h of filter changer 200. The intensity of the scattered light 204 passing through the chosen filter or filter mount may then be detected by a detector. The detector may output a signal related to the intensity of the detected light to the processor, which may be recorded by the processor in a memory. The processor may then determine a new desired orientation of wheel 201, and again record the signal of the detected scattered light 204 (for the same sample). The processor may automate a series of measurements (e.g. on a single sample), automatically changing the filter that scattered light passes through, to run a complete experiment. The processor may then process the measured data to produce a desired output.

Instrument 100 and/or filter changer 200 may be used to perform dynamic light scattering (DLS) and depolarised dynamic light scattering (DDLS) measurements. DLS measurements do not require the measurement of the polarisation of scattered light, whereas DDLS measurements do require the measurement of the polarisation of scattered light.

To perform DDLS measurements, a first and a second polarising filter may be placed into a filter changer, for example filter changer 200. In particular, the first and second polarising filters may be orientated so that the first polarising filter, when in the detection path 204, transmits only the vertically polarised component of scattered light and the second polarising filter, when in the detection path 204, transmits only the horizontally polarised component of scattered light. Scattered light that passes through the first optical polariser may be detected by the detector. The first optical polariser may then be moved out of the detection path 204, and the second optical polariser moved into the detection path 204—for example by rotating the wheel of the filter changer if the filter changer is similar to filter changer 200. The scattered light passing through the second polarising filter may then be detected by the detector. The measurements taken through the first polarising filter can be combined with those taken through the second polarising filter to determine the polarisation of the scattered light.

To perform DLS, the optical polarisers may not be required. The optical polarisers may therefore be removed from the detection path 204 to perform DLS. For example, filter changer 200 may be rotated so that the empty filter mount 202h is in the detection path 204. Scattered light may therefore be detected by the detector without any attenuation due to passing through a filter. Alternatively, if the sample fluoresces when illuminated by the light source, a fluorescence filter may be used to remove the fluorescence from the scattered light beam. The fluorescence filter may for example be a narrow band filter which only transmits light within ±1 nm of the wavelength of the light source. The fluorescence filter may for example be placed in a filter mount of filter changer, and moved into the illuminated position to perform DLS measurements. An instrument according to the first aspect may therefore be used to perform both DLS and DDLS measurements.

Alternatively or additionally, an instrument according to the first aspect, such as instrument 100, may be used to perform fluorescence correlation spectroscopy (FCS). For these measurements, a series of band-stop and band-pass filters may be required. These filters may be placed in a filter changer, and the appropriate filter moved into the illuminated position when required. The filter changer may contain, for example, a set of filters for FCS, as well as polarisation filters for DDLS measurements.

In some embodiments, the filter changer may comprise a filter that combines an optical polariser with at least one of a narrow band, band-stop or band-pass filter.

Figure 3:
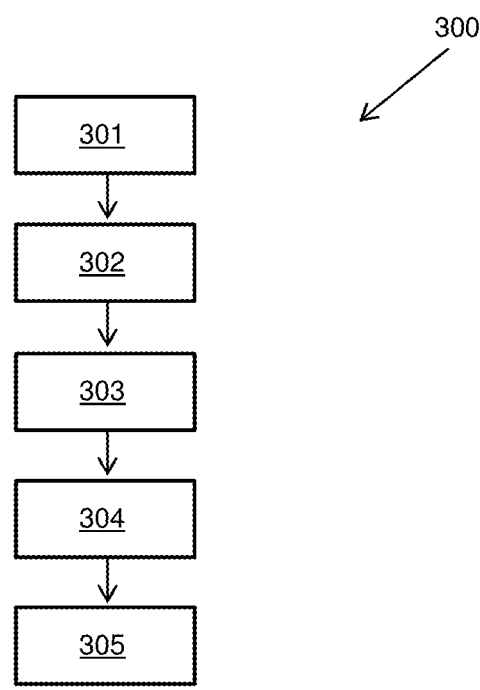
FIG. 3 is a representation of an exemplary method of measuring the characteristics of particles in a sample.

FIG. 3 illustrates a method of measuring the characteristics of particles in a sample, for example using the embodiments of the instrument described above. At step 301, a sample is placed in a sample cell. At step 302, the sample is illuminated with a light beam from a light source, for example light source 101, so as to produce scattered light by the interaction of the light beam with the sample. At step 303, an optical filter is moved into a scattered light detection path between the sample and a detector, for example any of detectors 105a-c, using a filter changer, for example filter changer 200. At step 304, the scattered light along the detection path is filtered using the optical filter, and finally at step 305 the scattered light that has passed through the optical filter is detected with the detector.

A number of filter components that are necessary to perform a specific analysis are not advantageous outside the context of that specific use, and may be disadvantageous or incompatible with another type of analysis. For example, a horizontal polariser may be necessary for a DDLS measurement, but the polariser will prevent a normal measurement for DLS, static light scattering (SLS) or electrophoretic light scattering (ELS). A narrow band filter may be useful for eliminating fluorescence when it may occur, but such a filter may result in unnecessary losses for samples that do not fluoresce. Such losses may limit the ability of the instrument to detect low levels of scattered light.

Furthermore, in some cases, a set of filters that can be changed during a measurement sequence is advantageous. For example, in the case of FCS it may be necessary to switch between a plurality of filters during a measurement sequence on a single sample. Similarly, a DDLS measurement may require switching between horizontally and vertically polarised scattered light during a measurement sequence on a single sample. In prior instruments, it has been necessary for an operator to supervise the instrument, and to switch filters manually at the appropriate time(s). Embodiments enable auto-titration measurements and auto-sampled measurements to be performed.

Other embodiments are intentionally within the scope of the appended claims.

The invention claimed is:

1. A particle characteristic measuring device, the device comprising:
   a light source that provides a light beam and that defines an illumination axis,
   a sample cell placed on the illumination axis,
   a scattered light detector positioned to receive scattered light along a detection path from a sample in the sample cell, the scattered light produced by interaction between the light beam and the sample, and
   a filter changer between the sample cell and the scattered light detector, the filter changer comprising:
      at least one optical filter comprising a first polarizing filter and a second polarizing filter, and
      an actuator that moves the at least one optical filter between:
         a first position in which the detection path does not pass through the optical filter;
         a second position in which the detection path passes through the first polarizing filter; and
         a third position in which the detection path passes through the second polarizing filter,
   wherein measurements taken through the first polarizing filter are combined with measurements taken through the second polarizing filter to determine a depolarized dynamic light scattering measurement.

2. The device of claim 1, comprising multiple optical filters and wherein the filter changer comprises a rotatable wheel, the wheel comprising multiple filter mounts that hold the multiple optical filters, and wherein the actuator rotates the wheel to move the filters between at least the first position and the second position.

3. The device of claim 1, wherein the at least one optical filter further comprises at least one of: a fluorescence filter, a band-stop filter, a band-pass filter, a high-pass filter and a low-pass filter.

4. The device of claim 1, comprising multiple optical filters and wherein the multiple optical filters comprise at least a first polarizing filter and a second polarizing filter.

5. The device of claim 4, wherein an axis of polarization of the first polarizing filter, when in the second position, is orthogonal to an axis of polarization of the second polarizing filter, when in the second position.

6. The device of claim 1, wherein the scattered light detector is positioned to receive back-scattered light, side-scattered light or forward-scattered light.

7. The device of claim 1, wherein the actuator comprises a motor.

8. The device of claim 1, wherein the device is configured to perform fluorescence correlation spectroscopy measurements.

9. The device of claim 1, comprising a controller, the controller operable to control the filter changer to move the at least one optical filter between the first, second, and third positions during characterization of a sample.

10. The device of claim 9, wherein the controller is operable, during characterization of a sample, to change which of the at least one filter is in the second position.

11. The device of claim 10, wherein the controller is operable, during characterization of a sample, to switch which of a first polarizing filter and a second polarizing filter are in the second position.

12. The device of claim 9, wherein the controller comprises a processor configured to control the operation of the filter changer.

13. The device of claim 1, comprising an auto-titrator and/or an auto-sampler.

14. A particle characteristic measuring method, the method comprising:
   placing a sample in a sample cell,
   illuminating the sample with a light beam from a light source to produce scattered light by interaction between the light beam and the sample,
   moving at least one optical filter comprising a first polarizing filter and a second polarizing filter into a scattered light detection path between the sample and a detector using a filter changer, the filter changer comprising an actuator that moves the at least one optical filter between:
      a first position in which the detection path does not pass through the optical filter;
      a second position in which the detection path passes through the first polarizing filter; and
      a third position in which the detection path passes through the second polarizing filter,
   filtering the scattered light along the detection path with the first optical filter comprising a first polarizing filter and a second polarizing filter; and
   detecting the scattered light that has passed through the first optical filter with the detector,
   wherein measurements taken through the first polarizing filter are combined with measurements taken through the second polarizing filter to determine a depolarized dynamic light scattering measurement.

15. The method of claim 14, comprising:
   moving a second optical filter into the detection path, and
   detecting the scattered light that has passed through the second optical filter with a detector.

16. The method of claim 15, wherein moving the second optical filter into the detection path comprises moving the first optical filter out of the detection path.

17. The method of claim 15, wherein the filter changer comprises a rotatable wheel, and wherein moving the second optical filter comprises rotating the wheel.

18. The method of claim 15, wherein the second optical filter comprises at least one of a polarizing filter, a fluorescence filter, a band-stop filter, a band-pass filter, a high-pass filter and a low-pass filter.

* * * * *